United States Patent [19]

Chou

[11] 4,190,724
[45] Feb. 26, 1980

[54] PROCESS FOR 3-EXOMETHYLENECEPHAM SULFOXIDES

[75] Inventor: Ta-Sen Chou, Indianapolis, Ind.

[73] Assignee: Eli Lilly and Company, Indianapolis, Ind.

[21] Appl. No.: 960,346

[22] Filed: Nov. 13, 1978

[51] Int. Cl.$^2$ ............................................. C07D 501/02
[52] U.S. Cl. ........................................ 544/16; 424/246
[58] Field of Search ........................................... 544/16

[56] References Cited

U.S. PATENT DOCUMENTS 4,052,387  10/1977  Kukolja ................................ 424/246

*Primary Examiner*—Nicholas S. Rizzo
*Attorney, Agent, or Firm*—William B. Scanlon; Arthur R. Whale

[57] ABSTRACT

Process for 3-exomethylenecepham sulfoxides comprising reacting a 2-chlorosulfinylazetidin-4-one ester with stannic chloride in the presence of oxo compounds, for example lower alkyl ethers and lower alkyl ketones, to form a stannic chloride complex with 2-chlorosulfinylazetidinone stabilized with said oxo compounds which, upon treatment with an hydroxy-containing compound such as methyl alcohol, decomposes providing said 3-exomethylenecepham sulfoxide.

10 Claims, No Drawings

4,190,724

PROCESS FOR 3-EXOMETHYLENECEPHAM SULFOXIDES

SUMMARY OF THE INVENTION

This invention relates to an improved process for the preparation of 3-exomethylenecepham sulfoxide esters. In particular, it relates to an improved process for converting a penicillin sulfoxide ester to a 3-exomethylenecepham sulfoxide ester via a 2-chlorosulfinylazetidin-4-one.

According to the process of this invention, a 2-chlorosulfinylazetidinone is reacted in an inert organic solvent with stannic chloride in the presence of an oxo ligand compound to provide an insoluble complex formed with the chlorosulfinylazetidinone, stannic chloride, and the oxo ligand compound. Cyclization of the 2-chlorosulfinylacetidinone occurs under heterogeneous conditions and it appears it may occur in the solid state at ordinary temperatures. Upon decomposition of the complex with an hydroxy-containing compound, the 3-exomethylenecepham sulfoxide ester separates from the complex in excellent yield.

The process improvement of this invention comprises the use of certain oxo ligand-forming compounds such as ethers and ketones, in the cyclization of a 2-chlorosulfinylazetidinone with the Friedel-Crafts catalyst stannic chloride. The oxo ligand compounds provide a more stable complex formed with the stannic chloride and the 2-chlorosulfinylazetidinone.

The improved process of this invention is advantageously carried out in conjunction with the preparation of a 2-chlorosulfinylazetidinone with a penicillin sulfoxide ester and, without isolating the 2-chlorosulfinylazetidinone, by proceeding directly to the stannic chloride complex formation in the cyclization to a 3-exomethylenecepham sulfoxide ester.

BACKGROUND OF THE INVENTION

The cyclization of 2-chlorosulfinylazetidinones with a Lewis acid-type Friedel-Crafts catalyst, a Bronsted proton acid-type Friedel-Crafts catalyst, or a metathetic cation-forming agent is described by Kukolja in U.S. Pat. No. 4,052,387. The cyclization results in the formation of a 3-exomethylenecepham sulfoxide ester. The process is useful in an overall two-step process for converting penicillin sulfoxide esters to the 3-exomethylenecepham ester sulfoxides which proceeds through the intermediate 2-chlorosulfinylazetidinones. The two-step process is illustrated in the following generalized reaction scheme.

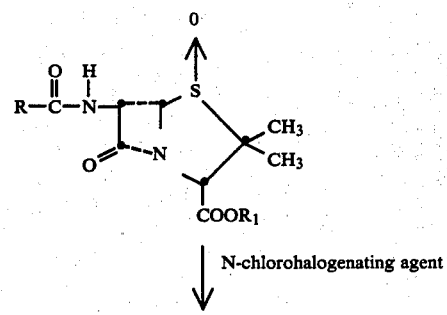

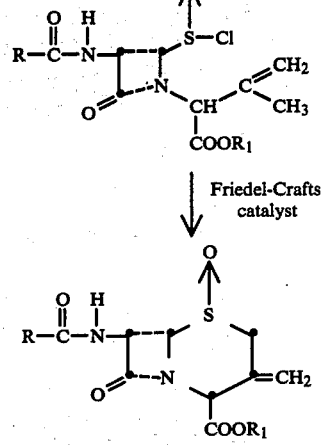

The preparation of 2-chlorosulfinylazetidinones and their use in the two-step process is described by Chou in U.S. Pat. No. 4,075,203. In co-pending application Ser. No. 960,347, filed this even date, there is described an improved process for the preparation of the 2-chlorosulfinylazetidinone intermediates which comprises the use of an insoluble poly(4-vinylpyridine)-divinylbenzene cross-linked co-polymer as the hydrogen chloride-binding agent, rather than the epoxide or epoxide-calcium oxide combinations as taught in U.S. Pat. No. 4,075,203.

The 2-chlorosulfinylazetidinone is employed as the intermediate in the Friedel-Crafts catalyzed cyclization to the 3-exomethylenecepham sulfoxide as shown above.

Accordingly, the above-described two-step process represents a method for preparing a cephalosporin-type compound from a penicillin-type compound which differs from the process described by Morin and Jackson in U.S. Pat. No. 3,275,626, wherein the acid catalyzed heat rearrangement of a penicillin sulfoxide ester to a desacetoxycephalosporin ester is described.

DETAILED DESCRIPTION

According to the process of this invention, a 2-chlorosulfinylazetidin-4-one represented by the following structural formula 1:

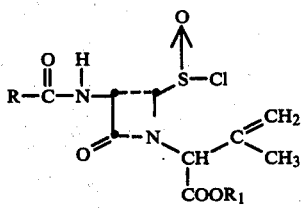

wherein R represents the residue of a carboxylic acid and $R_1$ is a carboxylic acid-protecting group, is reacted in an inert organic solvent under essentially anhydrous conditions with stannic chloride in the presence of an oxo ligand compound to provide an insoluble complex formed with the 2-chlorosulfinylazetidinone, stannic chloride, and the oxo ligand compound. The complex is then stirred for between about 3 and about 24 hours during which time the cyclization of 2-chlorosulfinylazetidinone to the 3-exomethylenecepham sulfoxide ester occurs in the solid state. The complex is then separated from the organic solvent, for example, by filtration, centrifugation, decantation, or other conventional means and is then treated with an hydroxy-containing compound such as a lower alcohol to effect the decomposition of the complex and provide the 3-exomethylenecepham sulfoxide ester represented by the following structural formula 2:

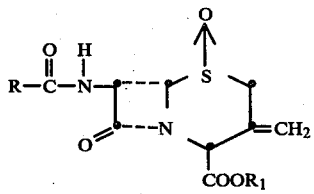

The process of this invention comprises the use of an oxo ligand-forming compound during the preparation of the stannic chloride-2-chlorosulfinylazetidinone complex. The oxo compound serves as a donor of an electron pair to form a coordinate covalent bond with a tin atom and thus forms part of the complex. Oxo compounds which can be used in the process of this invention are the lower alkyl ethers, cycloalkyl ethers, lower alkyl ketones, cycloalkyl ketones, tri-lower alkyl phosphine oxides, tricycloalkyl phosphine oxides, and triarylphosphine oxides. Oxo compounds which can be used in the process of this invention are represented by the following structural formulas.

Lower alkyl ethers 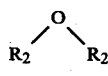 a

Cycloalkyl ethers 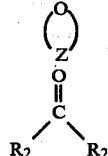 a'

Lower alkyl ketones 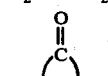 b

Cycloalkyl ketones 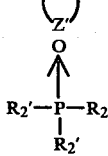 b'

Phosphine oxides  c where in the above formulas each $R_2$ is independently a straight or branched $C_1$–$C_4$ alkyl chain; $R_2'$ is independently a straight or branched $C_1$–$C_4$ alkyl chain, a $C_5$ or $C_6$ cycloalkyl group, phenyl or phenyl substituted by $C_1$–$C_4$ alkyl, $C_1$–$C_4$ alkoxy or halogen; Z is —$CH_2)_{m'}$, —$CH_2$—$CH_2$—O—$CH_2$— $CH_2$— or —$CH_2$—O—$CH_2$—$CH_2$—$CH_2$—, m is 4 or 5; and Z' is

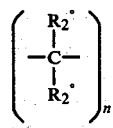

wherein each $R_2°$ is hydrogen or $C_1$–$C_4$ alkyl and n is an integral of from 3–6.

Illustrative of the lower alkyl ethers represented by formula a are dimethyl ether, diethyl ether, di-n-propyl ether, di-iso-propyl ether, di-n-butyl ether, methylethyl ether, methyl-n-propyl ether, methyl-sec-butyl ether, and the like. Representative of the cycloalkyl ethers of the formula a' are tetrahydrofuran, tetrahydropyran, 1,4-dioxane, and 1,3-dioxane. Illustrative of the lower alkyl ketones represented by the formula b are acetone, methyl ethyl ketone, diethyl ketone, di-n-propyl ketone, di-iso-propyl ketone, methyl-iso-propyl ketone, di-n-butyl ketone, di-sec-butyl ketone, methyl-iso-butyl ketone, and like lower alkyl ketones. Illustrative of the cycloalkyl ketones represented by the formula b' are cyclobutanone, cyclohexanone, cycloheptanone, 3-methyl-cyclohexanone, 3,4-diethylcyclopentanone, 3,5-dimethylcyclohexanone, 4-t-butylcyclohexanone, and like cycloalkyl and substituted cycloalkyl ketones. Illustrative of the lower alkyl, cycloalkyl, phenyl and substituted phenylphosphine oxides represented by the formula c are trimethylphosphine oxide, triethylphosphine oxide, tri-n-butylphosphine oxide, tri-n-propylphosphine oxide, tricyclohexylphosphine oxide, triphenylphosphine oxide, and the substituted triphenylphosphine oxides such as tri-(p-tolyl)phosphine oxide, tri-(p-chlorophenyl)phosphine oxide, tri-(p-bromophenyl)phosphine oxide, and like lower alkyl, cycloalkyl, phenyl and substituted phenylphosphine oxides.

The oxo compounds described above appear to serve two functions in the process of this invention. First, they coordinate via the electron pair on the oxygen atom with the tin atom of the stannic chloride to lower the reactivity of the tin halide towards the 2-chlorosulfinylazetidinone, and, secondly, they form a ligand with the stannic chloride-2-chlorosulfinyl azetidonine complex rendering the complex more stable. Apparently, the oxo ligand coordinates via a coordinate covalent bond with the central tin atom of the complex and thus prevents the deleterious effect of traces of moisture in the reaction medium which can lead to the destruction of the complex prior to cyclization. The oxo compounds thus permit the formation of a more stable complex in which the cyclization of the 2-chlorosulfinyl azetidinone to the 3-exomethylenecepham sulfoxide occurs.

In carrying out the process of this invention, the oxo compound can be added to the solution of the 2-chloroazetidinone prior to the addition of the stannic chloride, or, alternatively, the stannic chloride and the oxo compound can be mixed together in the inert organic solvent and added together to the solution of the 2-chloroazetidinone. It is preferable in the practice of this invention to add the oxo compound to the solution of the 2-chlorosulfinylazetidinone prior to the addition of stannic chloride.

Preferred oxo compounds of use in this invention are diethyl ether, acetone, and diethyl ketone.

The structure of the stannic chloride 2-chlorosulfinylazetidinone-oxo ligand complex has as yet not been determined. It appears, however, that the stannic chloride and the oxygen atom of the sulfinyl chloride group of the azetidinone are coordinately covalently bound and that 1-oxo compound forms a single coordinate covalent bond with the central tin atom. There are, however, other possibilities of bonding, for example, the oxygen atom of the acylamido group in the 3-position of the azetidinone may also form a coordinate covalent bond with the tin atom. Likewise, the oxygen atom of the ester group can possibly form a coordinate covalent bond with a tin atom.

Inert organic solvents which can be employed in the cyclization reaction of this invention are those solvents in which the 2-chlorosulfinylazetidinone and the oxo compound are soluble and in which the stannic chloride is at least partially soluble. The inert organic solvents are nonpolar and preferably are the aromatic hydrocarbon solvents such as benzene, chlorobenzene, toluene, chlorotoluene, the xylenes, and tetralin; the cycloalkyl hydrocarbon solvents such as cyclopentane, cyclohexane, and like hydrocarbon solvents. Prior to use in the process of this invention the solvent is dried by any of the conventional means for example by azeotropic distillation (binary-distillation) or by drying with a molecular sieve, or with one of the conventional drying agents such as calcium chloride, calcium sulfate, sodium sulfate, and the like. Preferably reagent grade solvents are employed.

The formation of the complex described herein is carried out at a temperature between about −15° C. and about 45° C. Preferably, and most conveniently, the complex is formed at a temperature between about 0° C. and about 20° C.

In carrying out the process of this invention, to a solution of the 2-chlorosulfinylazetidinone in an inert organic solvent such as benzene or toluene, is added with agitation between about 1 and 1.5 mole of oxo compound per mole of sulfinyl chloride. Thereafter, between about 2 and about 3 moles of stannic chloride per mole of sulfinyl chloride is added to the mixture. Commonly, the complex formation occurs rapidly. Generally, the complexes formed in the process of this invention are colored, ranging from light orange to red-orange to brown. The precipitated complex is then stirred in the reaction vessel for between about 3 and about 24 hours during which time the cyclization reaction is completed. Although in approximately 3 hours the cyclization is largely completed, the complex is allowed to stir for longer periods so that increased yield can be obtained. While the cyclization reaction is proceeding, there is no noticeable change in the complex. After stirring, the complex can be separated from the solvent, for example, by filtration or centrifugation or the solvent can be decanted from the complex, and the complex is then preferably washed with a suitable solvent such as petroleum ether, cyclohexane, toluene, diethyl ether, or with acetone. The washed complex can be stored in a suitable container or, preferably, it is decomposed to provide the 3-exomethylenecepham ester sulfoxide product.

The decomposition of the complex formed in the process of this invention is carried out by adding the complex to an hydroxy-containing compound, for example, a lower alcohol such as methyl alcohol or ethyl alcohol. The complex likewise can be decomposed with water or with an acid such as acetic acid or dilute hydrochloric acid; however, with these agents decomposition results in the formation of hydrogen chloride which can lead to untoward reactions with the product. Preferably, the complex is added to a lower alcohol such as methyl alcohol. The complex decomposes rapidly resulting in a slurry or suspension, usually of white to off-white color, of the 3-exomethylenecepham ester sulfoxide.

The 2-chlorosulfinylazetidin-4-one compounds represented by the above structural formula have been previously described and are prepared by the procedures described by Kukolja in U.S. Pat. No. 4,081,440, Mar. 28, 1978, and by Chou in U.S. Pat. No. 4,075,203, Feb. 21, 1978.

As was previously mentioned, R in the above formula 1 is the residue of a carboxylic acid. Preferred starting materials in the process of this invention are represented by the above formula I wherein R is hydrogen, $C_1$–$C_3$ alkyl, cyanomethyl, benzyloxy, 4-nitrobenzyloxy, t-butyloxy, 2,2,2-trichloroethoxy, 4-methoxybenzyloxy; or R is the group R' in which R' is phenyl or phenyl substituted by one or two halogen, protected hydroxy, nitro, cyano, trifluoromethyl, $C_1$–$C_4$ alkyl, or $C_1$–$C_4$ alkoxy; or R is a group of the formula R''—(O)$_m$—CH$_2$— in which R'' has the same meanings as R' as defined above, 1,4-cyclohexadienyl, 2-thienyl, or 3-thienyl; m is 0 or 1; with the limitation that when m is 1, R'' has the same meanings as R'; or R is a group of the formula R''—CH(W)— wherein R'' has the same meanings as defined above, and W is protected hydroxy or protected amino.

The compounds of the above formula 1 are referred to herein for convenience as 2-chlorosulfinylazetidin-4-ones. However, they are named formally as esters of a 1-azetidine substituted butenoic acid. For example, the compound represented by the formula 1 wherein R is benzyl and $R_1$ is t-butyl is named t-butyl 3-methyl-2-(2-chlorosulfinyl-4-oxo-3-phenylacetamido-1-azetidinyl)-3-butenoate.

Illustrative of the starting materials represented by the formula I which can be used in the process of this invention are:

t-Butyl 3-methyl-2-(2-chlorosulfinyl-4-oxo-3-phenylacetamido-1-azetidinyl)-3-butenoate, t-Butyl 3-methyl-2-(2-chlorosulfinyl-4-oxo-3-phenoxyacetamido-1-azetidinyl)-3-butenoate, Benzyl 3-methyl-2-(2-chlorosulfinyl-4-oxo-3-acetamido-1-azetidinyl)-3-butenoate, p-Nitrobenzyl 3-methyl-2-(2-chlorosulfinyl-4-oxo-3-formamido-1-azetidinyl)-3-butenoate, p-Methoxybenzyl 3-methyl-2-(2-chlorosulfinyl-4-oxo-3-cyanoacetamido-1-azetidinyl)-3-butenoate, Benzhydryl 3-methyl-2-(2-chlorosulfinyl-4-oxo-3-butyramido-1-azetidinyl)-3-butenoate, p-Nitrobenzyl 3-methyl-2-[2-chlorosulfinyl-4-oxo-3-(4-chlorophenoxyacetamido)-1-azetidinyl]-3-butenoate, 2,2,2-Trichloroethyl 3-methyl-2-[2-chlorosulfinyl-4-oxo-3-(2'-thienylacetamido)-1-azetidinyl]-3-butenoate, p-Nitrobenzyl 3-methyl-2-[2-chlorosulfinyl-4-oxo-3-(2'-thienylacetamido)-1-azetidinyl]-3-butenoate, Benzyl 3-methyl-2-(2-chlorosulfinyl-4-oxo-3-benzamido-1-azetidinyl)-3-butenoate, p-Nitrophenyl 3-methyl-2-(2-chlorosulfinyl-4-oxo-3-phenylacetamido-1-azetidinyl)-3-butenoate, Phenacyl 3-methyl-2-[2-chlorosulfinyl-4-oxo-3-(p-chlorobenzamido)-1-azetidinyl]-3-butenoate, Phthalimidomethyl 3-methyl-2-(2-chlorosulfinyl-4-oxo-3-phenoxyacetamido-1-azetidinyl)-3-butenoate, p-Nitrobenzyl 3-methyl-2-[2-chlorosulfinyl-4-oxo-3-(p-nitrophenylacetamido)-1-azetidinyl]-3-butenoate, 2,2,2-Trichloroethyl 3-methyl-2-(2-chlorosulfinyl-4-oxo-3-phenylacetamido-1-azetidinyl)-3-butenoate, p-Nitrobenzyl 3-methyl-2-[2-chlorosulfinyl-4-oxo-3-(α-benzhydryloxyphenylacetamido)-1-azetidinyl]-3-butenoate, and p-Nitrobenzyl 3-methyl-2-[2-chlorosulfinyl-4-oxo-3-(α-t-butyloxycarbonylamidophenylacetamido)-1-azetidinyl]-3-butenoate.

A preferred group of 2-chlorosulfinylazetidinones useful in the practice of this invention are represented by the formula 1 wherein R is 2-thienylmethyl, benzyl, or phenoxymethyl. The preferred starting materials are esters of 3-methyl-2-(2-chlorosulfinyl-4-oxo-3-phenylacetamido-1-azetidinyl)-3-butenoic acid, 3-methyl-2-[2-chlorosulfinyl-4-oxo-3-(2'-thienylacetamido)-1-azetidinyl]-3-butenoic acid, and 3-methyl-2-(2-chlorosulfinyl-4-oxo-3-phenoxyacetamido-1-azetidinyl)-3-butenoic acid. These are preferred starting materials in the process of this invention since they yield 3-exomethylenecepham sulfoxide esters which are particularly valuable intermediates in the preparation of antibiotic compounds.

As was noted above, the 2-chlorosulfinylazetidin-4-one ester compounds which are used as starting materials in the process of this invention are prepared by the process described by Chou in U.S. Pat. No. 4,075,203 and preferably by the improved process described by co-pending application Ser. No. 960,347, filed this even date. Advantageously, the improved process of this invention is carried out as the second step of the two-step process by which a penicillin sulfoxide ester is first converted to a 2-chlorosulfinylazetidinone which is, without isolation, employed in the process of this invention as described herein to form a 3-exomethylenecepham sulfoxide ester. Accordingly, a preferred embodiment of the process of this invention comprises carrying out the cyclization on unisolated 2-chlorosulfinylazetidinone prepared with a penicillin sulfoxide ester and an N-chlorinating agent in the presence of a poly(4-vinylpyridine)-divinylbenzene copolymer containing approximately 2–5% cross-linking as described in co-pending application Ser. No. 960,347, filed this even date.

In a preferred embodiment, p-nitrobenzyl 6-phenoxyacetamido-2,2-dimethylpenam-3-carboxylate-1-oxide is reacted in anhydrous toluene with approximately 1.1 molar equivalents of N-chlorophthalimide in the presence of between about 1 and about 3 grams per gram of penicillin sulfoxide of poly(4-vinylpyridine)-divinylbenzene cross-linked to the extent of between about 2 and about 5%. The reaction is carried out at the reflux temperature for about 100 minutes, the reaction suspension is filtered to remove the insoluble copolymer and phthalimide and the filtrate containing p-nitrobenzyl 3-methyl-2-(2-chlorosulfinyl-4-oxo-3-phenoxyacetamido-azetidinyl)-3-butenoate is cooled to a temperature between about 0° and 10° C. About 1 molar equivalent of diethyl ether is added to the cold filtrate followed by the addition of between about 2 and 2.5 molar equivalents of stannic chloride. With the addition of the stannic chloride, the sulfinyl chloride-stannic chlorideoxo ligand complex precipitates from the cold filtrate and is stirred in the solvent for between about 3 and about 24 hours to ensure complete formation of the complex. Thereafter, the complex is filtered, washed on the filter with a suitable solvent such as a hydrocarbon solvent, for example, pentane or hexane, and is then added slowly to methyl alcohol to effect the decomposition of the complex with formation of p-nitrobenzyl 7-phenoxyacetamido-3-exomethylenecepham-4-carboxylate-1-oxide. The suspension of the product is stirred for between 2 and about 4 hours and is then filtered. The filtered product is conveniently washed on the filter and is dried.

The product obtained in the process of this invention is generally obtained in such quality as to not require further purification prior to its use in the preparation of antibiotic compounds. However, the product, if needs be, can be recrystallized from a suitable solvent to enhance its purity.

The foregoing preferred embodiment of the process of this invention is illustrated in the following reaction scheme.

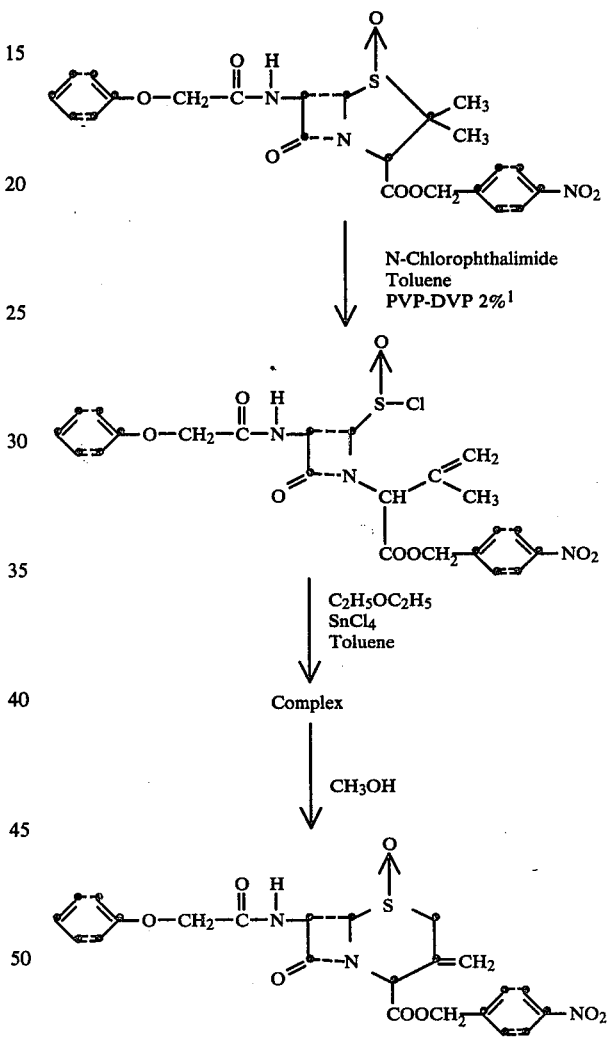

[1] Poly(4-vinylpyridine)-divinylbenzene with approximately 2% cross-linking.

The following Table I lists the yields of 3-exomethylenecepham sulfoxide obtained with representative oxo compounds present in the stannic chloride catalyzed cyclization of a preferred 2-chlorosulfinylazetidinone. In each instance, 50 g. of p-nitrobenzyl 6-phenoxyacetamido-2,2-dimethylpenam-3-carboxylate-1-oxide was converted to the corresponding 2-chlorosulfinylazetidinone p-nitrobenzyl ester with N-chlorophthalimide in toluene at the reflux temperature in the presence of poly(4-vinylpyridine)-divinylbenzene containing approximately 2% cross-linking. The insoluble polymer and phthalimide were filtered from the reaction medium, and the 2-chlorosulfinylazetidinone ester was cyclized with stannic chloride in the presence of about 1 mole of the oxo compound per mole of 2-chlorosulfinyl compound. In each instance, the complex formed was separated, washed, and decomposed with methyl alcohol. Column 3 in Table I lists the quality of the complex obtained in each instance. The melting point of the product, p-nitrobenzyl 7-phenoxyacetamido-3-exomethylenecephem-4-carboxylate-1-oxide observed in each instance is listed in column 4 in the table.

TABLE I

Oxo Compounds in Cyclization

| Oxo Compound Ethers | Percent Yield[1] | Percent Yield HPLC[2] | Condition of Complex | Melting Point (°C.) |
|---|---|---|---|---|
| Diethyl ether | 71.1 | 97.3 | Free flowing powder | 196.5 |
| Di-n-butyl ether | 65.8 | — | Sticky solid | 196.5–197 |
| Tetrahydrofuran | 61.9 | 96.2 | Free flowing powder | 193.5–194 |
| Tetrahydropyran | 60.9 | — | Slighlty gummy solid | 196–197 |
| Ketones | | | | |
| Acetone | 68.9 | 96.3 | Free flowing powder | 192–193 |
| Methylethyl ketone | 66.0 | 96.6 | Free flowing powder | 196–197 |
| Diethyl ketone | 68.0 | 96.1 | Free flowing powder | 195–196 |
| Methyl n-propyl ketone | 63.7 | 96.3 | Slightly sticky solid | 196.5–197 |
| Methyl iso-propyl ketone | 64.6 | 96.2 | Free flowing powder | 194.5–196 |

| Ketones Oxo Compound Ethers | Percent Yield[1] | Percent Yield HPLC[2] | Condition of Complex | Melting Point (°C.) |
|---|---|---|---|---|
| Methyl iso-butyl ketone | 63.0 | 95.1 | Free flowing powder | 195–196 |
| Cyclohexanone | 61.9 | — | Free flowing powder | 196–197 |
| Phosphine Oxides | | | | |
| Triphenylphosphine oxide | 99.0 | 58.8 | Free flowing powder | 192–197 |

[1]Percent yield on weight basis.
[2]High performance liquid chromatography.
Column: Merck RP18 of 25 cm × 4 mm i.d.
Column solvent: 530 ml. H$_2$O, 300 ml. THF, 150 ml. methanol, and 20 ml. acetic acid, containing 1.1 g. of octanesulfonic acid sodium per liter.
Rate: 2 ml./minute.
Sample size: 8 mg. per 25 ml. of anhydrous acetic acid or formic acid.

The 3-exomethylenecepham sulfoxide esters provided by the process are useful intermediates in the preparation of cephalosporin antibiotics. For example, the product is reacted with ozone to provide a 3-hydroxy-3-cephem sulfoxide ester, the latter is reduced to the sulfide form by methods conventional in the art and, the 3-hydroxy-3-cephem ester obtained is reacted either with diazomethane or with phosphorus trichloride in the presence of dimethylformamide to provide respectively a 3-methoxy-3-cephem ester or a 3-chloro-3-cepham ester. Deesterification of the esters affords respectively the 3-methoxy-3-cephem antibiotic which are described by Chauvette in U.S. Pat. Nos. 3,917,587 and 3,917,588 or the 3-chloro-3-cephem antibiotic which are described by Chauvette in U.S. Pat. Nos. 3,925,372 and 3,962,227.

The following examples further illustrate the process of this invention.

The following is an example of the preparation of a 2-chlorosulfinylazetidin-4-one ester in the presence of cross-linked poly(4-vinylpyridine)-divinylbenzene and the cyclization thereof with stannic chloride without the addition of an oxo compound of the invention.

EXAMPLE 1

Two liters of reagent grade toluene were refluxed for 2 hours under a Dean-Stark water trap until 200 ml. of liquid were collected from the trap and discarded. The heat was removed from the distillation and 25.0 g. of poly(4-vinylpyridine)-divinylbenzene (approximately 2% cross-linked), 50.2 g. of p-nitrobenzyl 6-phenoxyacetamido-2,2-dimethylpenam-3-carboxylate-1-oxide and 20 g. of N-chlorophthalimide were added. The suspension was quickly reheated to the reflux temperature and refluxing was continued with stirring for about 100 minutes. The reaction mixture was cooled to about 10° C. and was stirred for 10 minutes. The suspension was then filtered to remove the copolymer and phthalimide and the cold filtrate was added to a cold solution of 25 ml. of stannic chloride in 25 ml. of toluene. The light red-orange complex which formed was stirred at ice bath temperature for one hour, and for about 16 hours at room temperature. The color of the complex had changed to a light brown. The complex was filtered and washed with 200 ml. of pentane and dried. The complex was then added slowly to 300 ml. of methyl alcohol with formation of a suspension of the product, p-nitrobenzyl 7-phenoxyacetamido-3-exomethylenecepham-4-carboxylate-1-oxide. The suspension was stirred at ice bath temperature for 7 hours and filtered. The product was washed with 50 ml. of methyl alcohol, 50 ml. of diethyl ether, and dried in vacuo to yield 29.7 g. (59.5% yield) melting at about 187°–188.5° C.

The following example is a repeat of the preceding example except that the penicillin sulfoxide was employed at twice the concentration.

EXAMPLE 2

Two liters of reagent grade toluene were dried by refluxing under a Dean-Stark water trap until 200 ml. of liquid were collected from the water trap and discarded. The heat was removed from the distillation and 50 g. of poly(4-vinylpyridine)-divinylbenzene copolymer (approximately 2% cross-linking), 38.4 g. of N-chlorophthalimide, and 100.3 g. of p-nitrobenzyl 6-phenoxyacetamido-2,2-dimethylpenam-3-carboxylate-1-oxide were added to the hot toluene. The suspension was heated at the reflux temperature for 100 minutes and then cooled to 10° C. After stirring for 10 minutes the suspension was filtered into a cold solution of 50 ml. of stannic chloride in 50 ml. of toluene. The light orange complex which formed was stirred for one hour at ice bath temperature and for about 16 hours at room temperature. The complex was then filtered, washed with pentane, and partially dried on the filter. The complex was slowly added to 600 ml. of methyl alcohol with formation of a suspension of the product, p-nitrobenzyl 7-phenoxyacetamido-3-exomethylenecepham-4-carboxylate-1-oxide. The suspension was stirred at ice bath temperature for 7 hours and was filtered to collect 54.0 g. (54.1% yield) of the product melting at about 193.5°–194° C.

EXAMPLE 3

This example is an embodiment of the process of the invention carried out at the same concentration of starting material as in Example 2 (1 g./18 ml. toluene), and in which diethyl ether was employed as the oxo compound during the cyclization step.

Reagent grade toluene, 1800 ml., was dried as described in the preceding examples and while hot, 100.3 g. of p-nitrobenzyl 6-phenoxyacetamido-2,2-dimethylpenam-3-carboxylate-1-oxide, 50 g. of poly(4-vinylpyridine)divinylbenzene copolymer (approximately 2% cross-linking), and 38.4 g. of N-chlorophthalimide were added. The reaction suspension was heated at the reflux temperature for 100 minutes and was then cooled to 10° C. and stirred for 10 minutes. The cold suspension was filtered to remove the copolymer and phthalimide and the filtrate containing the 2-chlorosulfinylazetidin-4-one ester was cooled in an ice bath. First, 18.28 ml. of diethyl ether were added to the cold filtrate followed by the addition of 50 ml. of stannic chloride. The light orange-red complex which formed was stirred for 30 minutes at ice bath temperature and then for about 16 hours at room temperature. Little color change occurred in the complex.

The complex was filtered, washed on the filter with 400 ml. of hexane and dried in air. The complex was slowly added with stirring to 600 ml. of methyl alcohol with formation of a suspension of p-nitrobenzyl 7-phenoxyacetamido-3-exomethylenecepham-4-carboxylate-1-oxide.

The suspension was stirred for 4 hours at 0° C., and was filtered to collect the product. The product was washed with 100 ml. of methyl alcohol and dried in vacuo to yield 76.15 g. (76.2% yield) melting at about 194.5 to 195° C.

EXAMPLE 4

By employing the same penicillin sulfoxide ester, chlorinating agent and copolymer in the same quantities, and using the same volume of toluene as used in the preceding example, 12.9 ml. acetone were substituted for the diethyl ether of the preceding example to provide 72.63 g. (72.7% yield) of p-nitrobenzyl 7-phenoxyacetamido-3-exomethylenecepham-4-carboxylate-1-oxide melting at about 195° C.

EXAMPLE 5 p-Nitrobenzyl 7-phenylacetamido-3-exomethylenecepham-4-carboxylate-1-oxide

Reagent grade toluene, 300 ml. was distilled under a Dean-Stark water trap, and after the removal of 30 ml. of liquid from the trap the heat was removed and 2.5 g. of poly(4-vinylpyridine)-divinylbenzene (approximately 2% cross-linking) were added.

The suspension was refluxed a few minutes to remove any water which may have been added with the polymer. The heat was removed again and 7.28 g. of p-nitrobenzyl 6-phenylacetamido-2,2-dimethylpenam-3-carboxylate-1-oxide and 2.88 g. of N-chlorophthalimide were added while the suspension was hot. The mixture was then heated at the reflux temperature for 100 minutes. The dark suspension was cooled to 10° C. and filtered to remove the insoluble polymer and phthalimide. The filtrate containing p-nitrobenzyl 3-methyl-2-(2-chlorosulfinyl-4-oxo-3-phenylacetamido-1-azetidinyl)-3-butenoate was cooled in an ice bath and 1.37 ml. of diethyl ether were added followed by 3.75 ml. of stannic chloride. The brown complex which formed was stirred for 30 minutes in the cold and for about 16 hours at room temperature. The chocolate brown complex was filtered, washed with 60 ml. of hexane, and was then slowly added to 45 ml. of methyl alcohol to precipitate the product, p-nitrobenzyl 7-phenylacetamido-3-exomethylenecepham-4-carboxylate-1-oxide.

The suspension of product was stirred at ice bath temperature for 4 hours, was filtered and washed with 15 ml. of methyl alcohol and then in vacuo, yielding 4.3 g. (59.3% yield) melting at about 208°-208.5° C. after recrystallization from acetone.

EXAMPLE 6

2,2,2-Trichloroethyl 7-phenoxyacetamido-3-exomethylenecepham-4-carboxylate-1-oxide Toluene, 800 ml. was binary distilled under a Dean-Stark water trap by removing 80 ml. of liquid from the trap. The heat was discontinued and 6.68 g. of poly(4-vinylpyridine)divinylbenzene containing about 2 percent cross-linking, 20 g. of 2,2,2-trichloroethyl 6-phenoxyacetamido-2,2-dimethylpenam-3-carboxylate-1-oxide, and 7.74 g. of N-chlorophthalimide were added to the hot toluene. The suspension was heated at the reflux temperature for 100 minutes and was then cooled in an ice bath for about 20 minutes. The cold suspension was filtered to remove the copolymer and phthalimide and the filtrate was cooled in an ice bath. Diethyl ether, 3.66 ml., was added to the cold filtrate and, with stirring, 10 ml. of stannic chloride were added. After stirring for about 1 hour the complex began to precipitate. The suspension of dark complex was stirred overnight at room temperature and was filtered and washed with 80 ml. of hexane. The resulting tan sand like complex was added to 120 ml. of methyl alcohol and the mixture cooled in an ice bath. When after stirring for about 4 hours no product precipitated, the volume of the methyl alcohol was reduced to ⅓ its original volume by evaporation. The concentrate was dissolved in ethyl acetate and the solution washed twice with 5% aqueous sodium bicarbonate and with water and was then dried over magnesium sulfate. The dried solution was evaporated to dryness yielding 15.62 g. of the crude product 2,2,2-trichloroethyl 7-phenoxyacetamido-3-exomethylenecepham-4-carboxylate-1-oxide as a brown foam.

The product was suspended in 60 ml. of methyl alcohol and the suspension was warmed to about 50° C. to obtain a solution. On cooling to room temperature the product crystallized. The crystalline precipitate was filtered and dried yielding 1.9 g. of the product melting at about 143.5°-144° C.

NMR(CDCl$_3$):
 3.75 (q, 2H, J=4 and 18 cps, C$_2$H)
 4.58 (s, 2H, phenoxyacetyl methylene)
 4.83 (d, 2H, J=1.5 cps, trichloroethyl CH$_2$)
 4.95 (d, 1H, J=4.5 cps, C$_6$H)
 6.06 (q, 1H, J=4.5 and 11 cps, C$_7$H)
 5.53 (s, 1H, C$_4$H)
 5.42 and 5.87 (2s, =CH$_2$)
 8.16 (d, 1H, J=11 cps, NH) and
 6.83–7.50 (m, 5H, aromatic H) delta.

I claim:
1. In the process for preparing a 3-exomethylenecepham sulfoxide ester of the formula

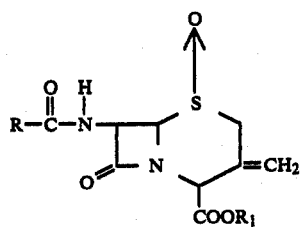

wherein R is the residue of a carboxylic acid and $R_1$ is a carboxylic acid protecting group, which comprises the steps, (a) adding to a solution of a 2-chlorosulfinylazetidin-4-one of the formula

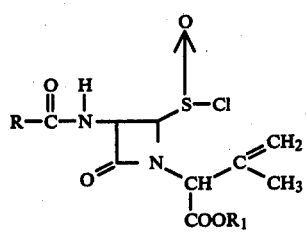

in an inert organic solvent under anhydrous conditions at a temperature between about $-15°$ C. and about $45°$ C., between about 2 and about 3 moles of stannic chloride per mole of said azetidinone; (b) separating the complex formed; and (c) decomposing said complex; the improvement which comprises adding the stannic chloride to said azetidinone solution in the presence of between about 1 and about 1.5 moles per mole of said azetidinone of an oxo compound selected from the group consisting of

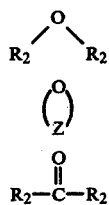

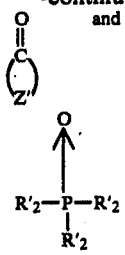

wherein the above formulas each $R_2$ is independently $C_1$–$C_4$ alkyl; each $R'_2$ is independently $C_1$–$C_4$ alkyl, $C_5$ to $C_6$ cycloalkyl, phenyl or phenyl substituted by $C_1$–$C_4$ alkyl, $C_1$–$C_4$ alkoxy, or halogen; Z is $(CH_2)_m$, $-CH_2-CH_2-O-CH_2-CH_2$, or $-CH_2-O-CH_2-CH_2-CH_2$; m is 4 or 5; and $Z'$ is

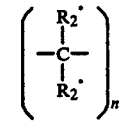

wherein each of $R_2°$ is hydrogen or $C_1$–$C_4$ alkyl, and n is 3 to 6.

2. The process of claim 1 wherein the complex is decomposed with a lower alcohol.

3. The process of claim 1 wherein the oxo compound is selected from the group consisting of diethyl ether, acetone and diethyl ketone.

4. The process of claim 1 wherein R is 2-thienylmethyl, benzyl, or phenoxymethyl.

5. The process of claim 4 wherein $R_1$ is p-nitrobenzyl, p-methoxybenzyl or benzyl.

6. The process of claim 5 wherein R is phenoxymethyl and $R_1$ is p-nitrobenzyl.

7. The process of claim 6 wherein the oxo compound is an oxo compound of the formulas $R_2$—O—$R_2$ and

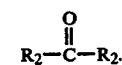

8. The process of claim 7 wherein the oxo compound is diethyl ether.

9. The process of claim 7 wherein the oxo compound is acetone.

10. The process of claims 8 and 9 wherein the inert organic solvent is toluene.

* * * * *